United States Patent [19]
Zobel

[11] Patent Number: 5,669,913
[45] Date of Patent: Sep. 23, 1997

[54] METHOD AND APPARATUS FOR SMOOTHING AN ANATOMICAL JOINT BEARING SURFACE DURING HEMI-JOINT REPLACEMENT

[76] Inventor: Robert A. Zobel, 3333 E. Downing, Mesa, Ariz. 85213

[21] Appl. No.: 577,446

[22] Filed: Dec. 22, 1995

[51] Int. Cl.⁶ .................................................. A61B 17/56
[52] U.S. Cl. ....................... 606/85; 606/76; 623/18; 623/54
[58] Field of Search ..................... 606/84, 85, 76; 623/54, 21

[56] References Cited

U.S. PATENT DOCUMENTS

| | | | |
|---|---|---|---|
| 3,760,427 | 9/1973 | Schultz | 3/1 |
| 3,965,489 | 6/1976 | Freeman et al. | 3/1.91 |
| 4,156,296 | 5/1979 | Johnson et al. | 3/1.91 |
| 4,621,637 | 11/1986 | Fishbein | 606/81 |
| 4,642,122 | 2/1987 | Steffee | 623/21 |
| 4,685,919 | 8/1987 | Niwa et al. | 623/21 |
| 4,787,908 | 11/1988 | Wyss et al. | 623/21 |
| 5,326,364 | 7/1994 | Clift, Jr. et al. | 623/21 |

*Primary Examiner*—Michael Buiz
*Assistant Examiner*—Julian W. Woo
*Attorney, Agent, or Firm*—Schmeister, Olsen & Watts

[57] ABSTRACT

A method and apparatus prepares a joint surface to receive a prosthetic joint implant during the replacement of a defective human joint. In particular the invention provides an implant preparation device that will smooth or alter a bearing surface of a first side of a joint before surgically attaching a joint implant to a second side of the joint. The implant or joint preparation device has an abrasive bearing surface that is used to smooth the bearing surface of the remaining natural joint. The method includes the additional surgical procedures of implanting the abrasive bearing surface joint preparation device into a first side of a joint, articulating the joint to remove all bearing surface deformities from a second side of the joint having a natural surface, removing the preparation device, cleaning the joint, and inserting the intended joint replacement part into the location used for the preparation device

12 Claims, 2 Drawing Sheets

METHOD AND APPARATUS FOR SMOOTHING AN ANATOMICAL JOINT BEARING SURFACE DURING HEMI-JOINT REPLACEMENT

BACKGROUND OF THE INVENTION

1. Field of the Invention

The present preferred embodiment of the invention generally relates to the replacement of joints in human beings. More specifically, the invention relates to tools and procedures for surgically replacing a human joint like found in the big toe.

2. Description of the Prior Art

The medical profession has used prosthetic devices for years to replace defective natural joints. One joint that is commonly replaced with a prosthetic device is the great toe (i.e., big toe) joint. Initially, hemi-joint replacements for the big toe were made of silicone taking advantage of the firm but resilient nature of the material. This method used a prosthetic device attached to the phalanx when the phalanx cartilage was degenerated but the metatarsal head was still intact. However, it was found that silicone was too soft for this intended purpose. The silicone surface breaks into small particles that are transported into the lymph system. With the recent concerns over the damaging effects of silicone in the human body that arose from documented problems with silicone breast implants, using silicone prosthetic devices for hemi-joint replacement is no longer a preferred solution.

Another method, similar to the hemi-joint silicone replacement, is total joint replacement, also using silicone. A prosthetic device for total joint replacement of the big toe has one end that is attached to the metatarsal while the other end is attached to the phalanx, and allows articulation between the two ends. This method was typically used when both the phalanx cartilage and the metatarsal head had been degenerated. Although this method has found limited success, it has been found that this method is not acceptable for all users, particularly those who propel off their big toe while walking or running, which commonly occurs during athletic activities. In addition, the concerns discussed above regarding the potential damaging effects of silicone in the body have caused medical practitioners to search for alternative materials.

Metal prosthetic devices, typically made of titanium or a titanium alloy, eliminate the health concerns of using silicone devices. When using metal prosthetic devices, either one or both sides of the joint are fitted with a metal implant. When a metal piece is used on only one side of the joint, it has been found that the head of the remaining natural joint wears out faster than the metal implant. Moreover, if both sides of the joint are replaced by the metal implants, then it has been found that there is a slow unavoidable dislocation of the joint (known as subluxation) and that there have been problems with increased joint stiffness.

As described above, various different types of toe implants (i.e., prosthetic devices) are known. Two different configurations of two-piece prosthetic devices for the great toe joint are disclosed in U.S. Pat. No. 4,642,122 (issued to Steffee on Feb. 10, 1987 and assigned to Laure Prosthetics, Inc.) and U.S. Pat. No. 4,156,296 (issued to Johnson et al. on May 29, 1979 and assigned to Bio-Dynamics, Inc.), both of which are incorporated herein by reference.

During surgery to replace half of a joint (i.e., hemi-joint replacement), the bone that receives the prosthetic device (or implant) is typically prepared to receive the implant. However, there are typically no steps performed to prepare the remaining anatomical half of the joint to mate to the new implant. It is not uncommon for the anatomical half of the joint to have bumps or other distortions in the cartilage and/or bone surface that will mate to the implant. Such bumps and distortions of the mating surface prevent the joint from operating in an optimal manner. Therefore, there existed a need to provide an apparatus and method for preparing an anatomical joint bearing surface to conform to the shape of an implant which will be surgically implanted to mate to the bearing surface.

SUMMARY OF THE PREFERRED EMBODIMENTS OF THE INVENTION

It is a feature of the invention to provide a surgical method and device used for implanting a joint replacement.

It is another feature of the invention to provide a method and apparatus for preparing a remaining natural joint to successfully adapt to a mated joint implant.

A further feature of the invention is to provide an implant preparation device that will smooth or alter a bearing surface of a first side of a joint before surgically attaching a joint implant to a second side of the joint.

Another feature of the invention is to provide a method of arthroplasty that is applicable to joints in the body, including fingers, toes, shoulders, hips, etc.

Yet, a further feature of the invention is to provide a joint preparation device that has an abrasive bearing surface that is used to smooth the bearing surface of the remaining natural joint.

Still, a feature of the invention is to provide a method of implanting an abrasive bearing surface joint preparation device into a first side of a joint, articulating the joint to remove all bearing surface deformities from a second side of a joint having a natural surface, removing the preparation device, cleaning the joint, and inserting the intended joint replacement part into the location used for the preparation device.

The invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, neither is it intended to be limiting as to the scope of the invention in any way.

Other features of the present invention will become more clear from the following detailed description of the invention, taken in conjunction with the accompanying drawings and claims, or may be learned by the practice of the invention.

BRIEF DESCRIPTION OF THE DRAWINGS

The preferred exemplary embodiment of the present invention will hereinafter be described in conjunction with the appended drawings, where like designations denote like elements, and.

Figure 1:
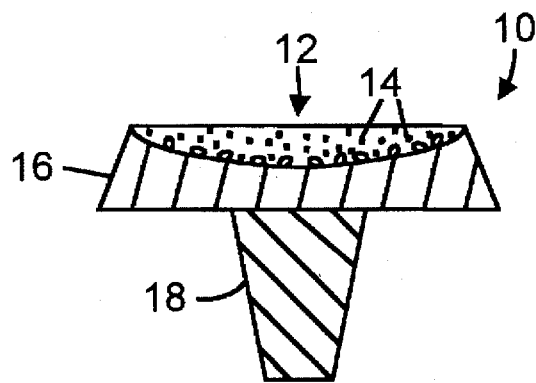
FIG. 1 is a cross-sectional side view of the concave abrasive bearing surface joint preparation device of FIG. 2 taken along the lines 1—1.

It is noted that the drawings of the invention are not to scale. The drawings are merely schematic representations, not intended to portray specific parameters of the invention. The drawings are intended to depict only typical embodiments of the preferred embodiment of the invention, and therefore should not be considered as limiting the scope of the invention. The invention will be described with additional specificity and detail through the use of the accompanying drawings.

DETAILED DESCRIPTION OF A PREFERRED EXEMPLARY EMBODIMENT

For the purposes of promoting an understanding of the principles of the invention, reference will now be made to the preferred embodiment of the invention as illustrated in the drawings and specific language will be used to describe the same. It will nevertheless be understood that no limitation of the scope of the invention is thereby intended.

Figure 2:
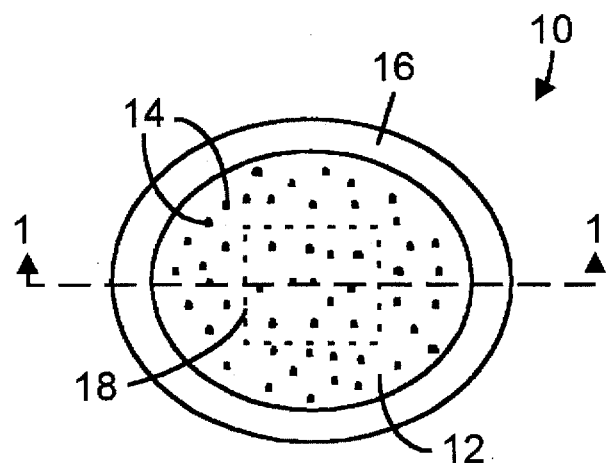
FIG. 2 is a top view of a concave abrasive bearing surface joint preparation device.

Referring to FIGS. 1 and 2, a joint preparation device 10 has a concave abrasive surface for preparing a portion of a joint to mate to a joint implant or prosthesis. Abrasive surface 12 is placed upon a support collar 16 forming a head part that is connected to attaching stem 18. Device 10 is generally placed in the socket side of a ball and socket joint. Device 10 has attaching stem 18 connected to abrasive surface 12 via support collar 16.

Figure 3:
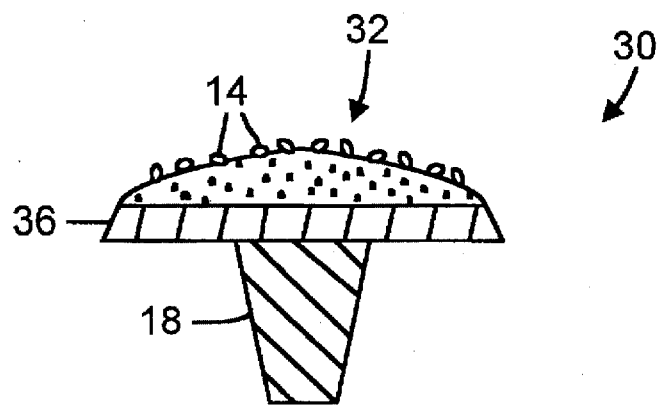
FIG. 3 is a cross-sectional side view of a convex abrasive bearing surface joint preparation device.

Referring to FIG. 3, a different configuration of a joint preparation device 30 in accordance with the present invention has a convex abrasive surface 32. Device 30 may generally be placed in the ball side of a ball and socket joint. Device 30 has a partially spherical abrasive surface 32. Abrasive material or grit 14 is located upon abrasive surface 32. Support collar 36 connects abrasive surface 32 to attaching stem 18. Stem 18 is positioned approximately in the center of support collar 36 and is perpendicular thereto as illustrated. In a preferred embodiment, stem 18 is an integral part of device 30.

Figure 4:
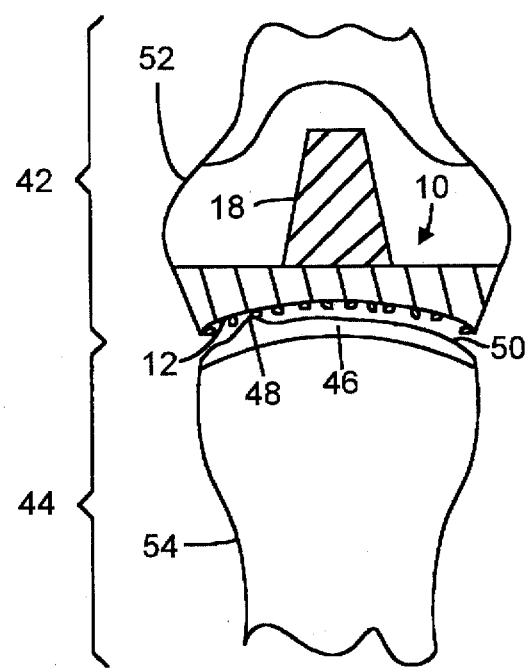
FIG. 4 is a skeletal representation of a side view of a joint incorporating a concave abrasive bearing surface joint preparation device.

FIG. 4 is a skeletal representation of a side view of a joint 40 incorporating the concave abrasive bearing surface joint preparation device 10. Joint 40 has a first side 42 and a second side 44, with corresponding first bone 52 and second bone 54. Second bone 54 typically has a cartilage layer 46. Cartilage 46 may contain one or more deformities (e.g., bump 48 of FIG. 4) on bearing surface 50 that needs to be removed for proper fit for a joint implant. The first side 42 was the damaged portion of the joint and thus has been surgically modified to fit preparation device 10 therein. The attachment stem 18 is implanted into the bone 52 on the first side of joint 40. The length of stem 18 must be sufficient to allow the preparation device 10 to be anchored into bone 52. The stem 18 may extend into the medullary canal of the bone in some instances to accomplish sufficient device anchoring.

Figure 5:
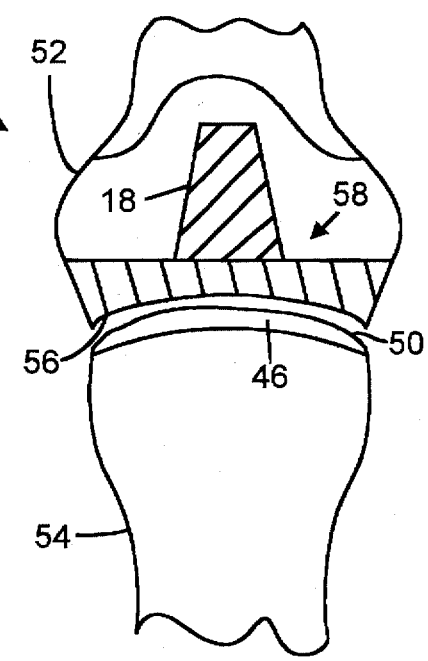
FIG. 5 is a skeletal representation of a side view of the joint shown in FIG. 4 incorporating a smooth convex bearing surface joint replacement.

FIG. 5 is a skeletal representation of a side view of a joint 40 incorporating a prosthesis 58 that has a smooth concave bearing surface. Joint 40 has prosthesis 58 fitted into the created cavity located on the first side 42 of joint 40. The cartilage 46 has a bearing surface 50 that will contact the smooth part-spherical bearing surface 56 of prosthesis 58. Stem 18 typically will be inserted and cemented into the cavity previously prepared for preparation device 10.

In operation, the preferred embodiment of the invention anticipates using any known standard operating procedures in performing the replacement of a defective joint. However, there is included the following extra procedures.

In reference to both FIGS. 4 and 5, after bone 52 has been properly excavated to create a cavity for securely fitting joint implant 58, preparation device 10 is inserted into the created cavity. The joint is then gently articulated in the full range of proper motion. In this fashion, the abrasive surface 12 of preparation device 10 will perform a chondroplasty by smoothing out any aberrations or deformities (e.g., 48) residing on the cartilage bearing surface 50. Next, preparation device 10 is removed and the joint is cleaned and irrigated to remove all debris or particles. Thereafter, joint implant 58 is surgically inserted into the created cavity following standard operating procedures.

Best Mode

While the description above relates to replacement of either portion of any ball and socket type joint in the human body, the best mode is directed to a hemi-joint replacement for a human great toe joint. A human great toe has a proximal phalanx that articulates on a metatarsal. A hemi-joint replacement of the great toe joint is typical when the socket portion of the proximal phalanx has deteriorated but the metatarsal head is largely intact. Referring to FIGS. 4 and 5, for the specific case of a hemi-joint replacement for a great toe joint 40, bone 52 represents the proximal phalanx while bone 54 represents the metatarsal. Metatarsal 54 typically has a cartilage layer 46 covering its bearing surface 50. Note, however, that the present invention applies even if cartilage layer 46 on metatarsal 54 has been deteriorated or is gone altogether.

The surgical procedure in accordance with the present invention begins by making an incision above the great toe joint such that the great toe joint is exposed. The damaged portion of proximal phalanx 52 is then removed, typically by making a cut normal to the longitudinal axis of proximal phalanx 52. The cut is made to accommodate an implant 58 which will replace the degenerated portion Of proximal phalanx 52. The medullary canal of proximal phalanx 52 is then enlarged to create a cavity that will receive stem portion 18 of implant 58. A preparation device 10 has a suitable size and shape similar to the size and shape of implant 58, with a substantially identical stem portion 18. Stem 18 of preparation device 10 is then placed within the cavity of proximal phalanx 52.

A chondroplasty is then suitably performed by articulating proximal phalanx 52 in all ranges of motion, placing pressure on the proximal phalanx such that abrasive surface 12 of preparation device 10 rubs off protrusions (e.g., 48 of FIG. 4) on bearing surface 50 of metatarsal 54 to provide a smooth mating surface for implant 58. Once the chondroplasty is completed, preparation device 10 is removed. The joint is then irrigated to remove debris, and implant 58 is then placed into proximal phalanx 52 and secured in place, and the incision is then closed. A smooth bearing portion 56 of implant 58 now slides easily on bearing surface 50 of metatarsal 54, resulting in greatly improved performance of joint 40.

Remarks about the Preferred Embodiment of the Invention

It is noted that preparation device 10 is specifically selected to have the same shape and size as the intended joint implant 58.

It is further noted that by articulating the joint with the joint preparation device 10 prior to implanting the joint implant, it has been found that the prior post surgical problems previously associated with joint replacements have been relatively eliminated. Thus, by removing minor deformities on the cartilage surface 50, the joint has been properly prepared to successfully mate to the new joint implant 58.

A skilled artisan will know that minor deformities are generally any shape on the mated natural joint that will not be an exact fit to the joint implant top surface 56. Therefore, even depressions in the mated natural joint surface are intended to be removed by use of the preferred embodiment.

One skilled in the art of joint implants will easily understand that the preferred embodiment of the operating procedure and preparation devices are readily applicable to many types of joints and to all surfaces of the joints that may receive joint implants.

Further, one skilled in the art will understand that the preferred embodiment will equally work on joints were the cartilage has been removed and the surface of the bone will be mated to the joint implant. In this situation, the preparation device will smooth out the surface of the bone in preparation to receiving the joint implant.

Variations in the Preferred Embodiment

Although this embodiment discusses only two shapes of joint replacements, it is contemplated to apply the preferred embodiment to all known shapes and types of joint replacements. For example, the preferred embodiment could be applied to a Swanson condylar implant, Swanson Great Toe implant, or Angled Great Toe Weil Modification designs. Each of these implants can be purchased at Dow Coming Wright, located at 5677 Airline Rd. Arlington, Tenn. 38002.

Similar to the joint replacements, it is contemplated to use the preferred embodiment on all manner of joints in the body. For example, as described above, first bone 52 could be the phalanx of the big toe and second bone 54 could be the metatarsal of the big toe. Similarly, this embodiment would work on the shoulder joints, the finger joints, the hip joints, the elbow joints, etc. While a concave preparation device such as device 10 of FIGS. 1, 2 and 4 is used to smooth an anatomical ball portion of a ball and socket joint, in like manner a convex preparation device 30 (FIG. 3) could be used in similar fashion to smooth an anatomical socket portion of a ball and socket joint.

The current embodiment of the invention also anticipates the use of any type of material in manufacturing the preferred embodiment.

One skilled in the art will also understand that the preparation devices could be made of two or more separate pieces. For example, stem 18 could be separated from the collar and bearing surface assemblies, and could be attached by any know means such as screws. In addition, while stem 18, collar 16, and abrasive surface 12 are shown in the figures as separate portions of device 10, these different features are shown separately for purposes of illustrating and describing the invention, and in the preferred embodiment device 10 is formed in a single piece.

Although the preferred embodiment discussion have discussed using the preparation device 10 in a single step it is contemplated to use multiple steps and preparation devices in a single operation. For example, it could be advantageous to use a first preparation device that has a course abrasive surface and a second preparation device having a finer abrasive surface.

The preferred embodiment discusses the use of grit or abrasive material. Thus, the grit 14 size plays a significant role in the preparation of the remaining natural joint surface. However, the invention contemplates any means of creating a rough surface on the preparation device 10 sufficient to perform the intended smoothing operation. For example, grooves or ridges may be formed on the bearing surface of the joint preparation device to create an abrasive surface.

It is contemplated to make the preparation device 10 out of any known surgically compatible material. For example, titanium, gortex, or silicone may be suitable.

Additionally, it is contemplated to form different parts of the preparation device out of differing materials. For example, the grit 14 out of diamond, the top surface 12 out of titanium, and the stem 18 out of silicone.

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A surgical method for implanting a prosthesis into a first bone located on a first side of a joint to mate to a second bone located on a second side of the joint, the method including a step of smoothing a bearing surface of the second bone, the smoothing step comprising the steps of:
    a) removing a portion of the first bone adjacent the joint to create a cavity therein;
    b) inserting a joint preparation device into the cavity so that an abrasive surface of the preparation device is juxtaposed to a joint surface located on the second bone; and
    c) articulating the joint to smooth the joint surface of the second bone to conform to the abrasive surface of the joint preparation device.

2. The method of claim 1, further comprising the steps of:
    d) removing the joint preparation device; and
    e) inserting the prosthesis into the cavity.

3. The method of claim 1, further comprising the step of cleaning the joint of all debris created from the articulating step.

4. The method of claim 1, wherein the cavity is shaped and sized to snugly fit the prosthesis into the first bone.

5. The method of claim 1, wherein the surface of the second bone includes cartilage.

6. The method of claim 1, wherein the abrasive surface of the joint preparation device has a size and shape that is relatively similar to a smooth top surface of the prosthesis.

7. The method of claim 6, wherein a shape of the abrasive surface of the preparation device and the smooth top surface of the prosthesis are both concave.

8. The method of claim 6, wherein a shape of the abrasive surface of the preparation device and the smooth top surface of the prosthesis are both convex.

9. The method of claim 1, wherein the joint is a toe joint and the first bone is a phalanx and the second bone is a metatarsal.

10. The method of claim 1, wherein the prosthesis is a portion of an artificial joint.

11. The method of claim 2, further including after step d) and before step e) the steps of:
    i) inserting a second preparation device into the cavity so that a second abrasive top surface of the second preparation device is juxtaposed to a joint surface located on the second bone, wherein the second abrasive top surface is less abrasive than the abrasive surface of the joint preparation device;
    ii) articulating the joint to smooth the second bone joint surface to conform to the abrasive surface of the second joint preparation device; and
    iii) removing the second joint preparation device.

12. A method for hemi-joint replacement of a human great toe joint, the great toe joint comprising a proximal phalanx that articulates on a metatarsal, the method comprising the steps of:
    a) making an incision over the joint;
    b) removing a portion of the proximal phalanx to create a cavity therein;
    c) inserting a preparation device into the cavity so that an abrasive surface of the preparation device is juxtaposed to a top surface of the metatarsal;
    d) articulating the proximal phalanx so the abrasive surface of the preparation device comes in contact with the top surface of the metatarsal, the articulating motion abrasively removing material from the metatarsal;
    e) removing the joint preparation device;
    f) inserting an implant into the cavity; and
    g) closing the incision over the joint.

\* \* \* \* \*